US009283847B2

(12) United States Patent
Riley, Sr. et al.

(10) Patent No.: US 9,283,847 B2
(45) Date of Patent: Mar. 15, 2016

(54) SYSTEM AND METHOD TO MONITOR AND ALERT VEHICLE OPERATOR OF IMPAIRMENT

(71) Applicant: STATE FARM MUTUAL AUTOMOBILE INSURANCE COMPANY, Bloomington, IL (US)

(72) Inventors: Matthew Eric Riley, Sr., Heyworth, IL (US); Gregory Dwayne Carter, Bloomington, IL (US); James M. Freeman, Normal, IL (US); Vaidya Balasubramanian Pillai, Springfield, IL (US); Jason Chang, Roselle, IL (US); David W. Thurber, Sherman, IL (US)

(73) Assignee: STATE FARM MUTUAL AUTOMOBILE INSURANCE COMPANY, Bloomington, IL (US)

( * ) Notice: Subject to any disclaimer, the term of this patent is extended or adjusted under 35 U.S.C. 154(b) by 0 days.

(21) Appl. No.: 14/269,490

(22) Filed: May 5, 2014

(65) Prior Publication Data

US 2015/0314681 A1  Nov. 5, 2015

(51) Int. Cl.
*G08B 23/00* (2006.01)
*B60K 28/06* (2006.01)
*B60W 40/08* (2012.01)

(52) U.S. Cl.
CPC ............... *B60K 28/066* (2013.01); *B60W 40/08* (2013.01); *B60W 2040/0818* (2013.01); *B60W 2040/0827* (2013.01); *B60Y 2400/902* (2013.01)

(58) Field of Classification Search
CPC ........ G08B 21/00; G08B 21/02; G08B 21/06; G08B 21/0438; G08B 21/0469; B60W 40/08; B60W 2540/22–2540/26; B60W 2040/0818–2040/0872; B60W 30/00; B60W 40/09; B60W 30/02; B60W 50/14; B60W 30/08; G08G 1/166
USPC ................. 340/573.1, 575, 576, 691.1, 691.7
See application file for complete search history.

(56) References Cited

U.S. PATENT DOCUMENTS 4,218,763 A * 8/1980 Kelley et al. .................. 340/429
4,565,997 A * 1/1986 Seko et al. .................... 340/576

(Continued)

OTHER PUBLICATIONS

Fields et al., U.S. Appl. No. 14/201,491, filed Mar. 7, 2014.

(Continued)

*Primary Examiner* — Steven Lim
*Assistant Examiner* — Ryan Sherwin
(74) *Attorney, Agent, or Firm* — Marshall, Gerstein & Borun LLP; Randall G. Rueth

(57) ABSTRACT

The method, system, and computer-readable medium facilitates monitoring a vehicle operator during the course of vehicle operation to determine whether the vehicle operator is impaired (e.g., distracted, drowsy, intoxicated) and alerting the vehicle operator using a haptic alert delivered by a wearable computing device worn by the vehicle operator when impairment is detected. The method, system, and computer-readable medium may monitor the vehicle operator, the environment surrounding the vehicle, and/or forces acting on the vehicle using a variety of sensors, including optical sensors or accelerometers. In particular, optical sensors may monitor the vehicle operator to detect eye blinks, head nods, head rotations, and/or gaze fixation. Optical sensors may also monitor the road ahead of the vehicle to detect lane deviation, lane centering, and time to collision. Accelerometers may detect acceleration in the direction of vehicle travel and/or lateral acceleration.

20 Claims, 5 Drawing Sheets

(56) References Cited

U.S. PATENT DOCUMENTS

| | | | |
|---|---|---|---|
| 6,031,354 A * | 2/2000 | Wiley et al. | 320/116 |
| 6,313,749 B1 * | 11/2001 | Horne | G08B 21/06 340/575 |
| 6,477,117 B1 * | 11/2002 | Narayanaswami et al. | 368/251 |
| 6,661,345 B1 | 12/2003 | Bevan et al. | |
| 7,027,621 B1 * | 4/2006 | Prokoski | 382/118 |
| 7,054,723 B2 | 5/2006 | Seto et al. | |
| 7,138,922 B2 | 11/2006 | Strumolo et al. | |
| 7,149,533 B2 * | 12/2006 | Laird et al. | 455/456.3 |
| 7,719,431 B2 | 5/2010 | Bolourchi | |
| 7,792,328 B2 * | 9/2010 | Albertson et al. | 382/104 |
| 7,835,834 B2 | 11/2010 | Smith et al. | |
| 8,009,051 B2 | 8/2011 | Omi | |
| 8,040,247 B2 * | 10/2011 | Gunaratne | 340/575 |
| 8,876,535 B2 | 11/2014 | Fields et al. | |
| 2004/0017106 A1 | 1/2004 | Aizawa et al. | |
| 2004/0090334 A1 | 5/2004 | Zhang et al. | |
| 2006/0232430 A1 | 10/2006 | Takaoka et al. | |
| 2007/0080816 A1 | 4/2007 | Haque et al. | |
| 2007/0159344 A1 | 7/2007 | Kisacanin | |
| 2008/0291008 A1 | 11/2008 | Jeon | |
| 2010/0131304 A1 | 5/2010 | Collopy et al. | |
| 2010/0214087 A1 | 8/2010 | Nakagoshi et al. | |
| 2011/0304465 A1 | 12/2011 | Boult et al. | |
| 2012/0083668 A1 * | 4/2012 | Pradeep et al. | 600/300 |
| 2012/0316406 A1 * | 12/2012 | Rahman et al. | 600/301 |
| 2013/0038437 A1 | 2/2013 | Talati et al. | |
| 2013/0073115 A1 | 3/2013 | Levin et al. | |
| 2013/0227409 A1 * | 8/2013 | Das et al. | 715/702 |
| 2013/0307786 A1 * | 11/2013 | Heubel | 345/173 |
| 2014/0059066 A1 | 2/2014 | Koloskov | |
| 2014/0167967 A1 | 6/2014 | He et al. | |
| 2014/0168399 A1 | 6/2014 | Plummer et al. | |
| 2014/0172467 A1 | 6/2014 | He et al. | |
| 2014/0218187 A1 | 8/2014 | Chun et al. | |
| 2014/0240132 A1 * | 8/2014 | Bychkov | 340/576 |
| 2014/0309864 A1 * | 10/2014 | Ricci | 701/36 |
| 2015/0070265 A1 | 3/2015 | Cruz-Hernandez et al. | 345/156 |
| 2015/0302719 A1 * | 10/2015 | Mroszczak | G08B 21/0446 340/539.12 |

OTHER PUBLICATIONS

Fields et al., U.S. Appl. No. 14/255,934, filed Apr. 17, 2014.
Fields et al., U.S. Appl. No. 14/511,712, filed Oct. 10, 2014.
Fields et al., U.S. Appl. No. 14/511,750, filed Oct. 10, 2014.

* cited by examiner

SYSTEM AND METHOD TO MONITOR AND ALERT VEHICLE OPERATOR OF IMPAIRMENT

TECHNICAL FIELD

The present disclosure generally relates to a system and a method for alerting a vehicle operator of vehicle operator impairment and, more particularly, to a device that can determine operator impairment and provide a haptic alert.

BACKGROUND

Every year many vehicle accidents are caused by impaired vehicle operators. One common kind of impaired vehicle operation is drowsy driving. If the vehicle operator falls asleep for even a second while driving, the results can be disastrous. Another common kind of impaired vehicle operation is distracted driving. Modern motor vehicles come equipped with any number of distractions including stereos, air-conditioners, navigation systems, etc. Furthermore, a vehicle operator can be distracted by another passenger or by articles the vehicle operator brings into the vehicle (e.g., a mobile telephone, book, etc.).

SUMMARY

The present application discloses a method, system, and computer-readable medium storing instructions for alerting a vehicle operator of impairment. One embodiment includes a computer-implemented method including receiving data about potential vehicle operator impairment from one or more sensors, processing the sensor data to determine whether the vehicle operator is impaired, and delivering a haptic alert to the vehicle operator using a wearable computing device when the vehicle operator is determined to be impaired. An alternative embodiment includes a computer system having a processor, sensor, wearable computing device, and program memory storing instructions that when executed by the processor cause the computer system to receive sensor data regarding the vehicle operator, process the sensor data to determine whether the vehicle operator is impaired, and deliver a haptic alert to the vehicle operator using a wearable computing device when it is determined that the vehicle operator is impaired. Another alternative embodiment includes a tangible, non-transitory computer-readable medium storing instructions that when executed by a processor of a computer system cause the computer system to receive sensor data regarding the vehicle operator, process the sensor data to determine whether the vehicle operator is impaired, and deliver a haptic alert to the vehicle operator using a wearable computing device when it is determined that the vehicle operator is impaired.

The wearable computing device may be any computing device capable of providing a haptic alert and capable of being used while being worn by the user, such as a smart watch or computer-enhanced eyeglasses. The sensors may include any electronic device capable of providing sensor data regarding the vehicle operator, vehicle motion, or the vehicle's environment. In addition to other information, the sensors may be used to monitor the following: vehicle operator head nods, vehicle operator scanning frequency, vehicle operator gaze fixation, vehicle operator mirror checking, vehicle operator head rotations, vehicle operator arm movement, vehicle operator skin conductance, vehicle operator temperature, vehicle operator pulse rate, vehicle lane deviation, vehicle swerving, vehicle lane centering, vehicle acceleration along a single axis or multiple axes, and vehicle distance to other objects.

In one embodiment, the wearable computing device may be communicatively connected to a control device, such as a smart phone or on-board computer. The control device may receive sensor data, process the sensor data to determine whether a vehicle operator is impaired, and control the delivery of the haptic alert by the wearable computing device. Additionally, the control device may communicate with one or more servers, which may perform part or all of the functions of the control device.

In one embodiment, the haptic alert may be supplemented by additional audible or visual alerts, but a haptic alert is particularly effective in a noisy environment or where a vehicle operator's eyes are closed. The type of haptic or other alert displayed may be selected from a database based on the sensor data. Additionally, the alert may be disabled automatically after a certain time-out period has passed or earlier by a shut-off command from the vehicle operator. The method, system, or instructions may also suppress the delivery of the alert until a certain reset period has passed following the delivery of the previous alert.

BRIEF DESCRIPTION OF THE DRAWINGS

The figures described below depict various aspects of the applications, methods, and systems disclosed herein. It should be understood that each figure depicts an embodiment of a particular aspect of the disclosed applications, systems and methods, and that each of the figures is intended to accord with a possible embodiment thereof. Furthermore, wherever possible, the following description refers to the reference numerals included in the following figures, in which features depicted in multiple figures are designated with consistent reference numerals.

DETAILED DESCRIPTION

Although the following text sets forth a detailed description of numerous different embodiments, it should be understood that the legal scope of the invention is defined by the words of the claims set forth at the end of this patent. The detailed description is to be construed as exemplary only and does not describe every possible embodiment, as describing every possible embodiment would be impractical, if not impossible. One could implement numerous alternate embodiments, using either current technology or technology developed after the filing date of this patent, which would still fall within the scope of the claims.

It should also be understood that, unless a term is expressly defined in this patent using the sentence "As used herein, the term '_____' is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this patent is referred to in this patent in a manner consistent with a single meaning, that is done for sake of clarity only so as to not confuse the reader, and it is not intended that such claim term be limited, by implication or otherwise, to that single meaning. Finally, unless a claim element is defined by reciting the word "means" and a function without the recital of any structure, it is not intended that the scope of any claim element be interpreted based on the application of 35 U.S.C. §112(f).

As used herein, the term "impairment" refers to any of a number of conditions that may reduce vehicle operator performance. A vehicle operator may be impaired if the vehicle operator is drowsy, asleep, distracted, intoxicated, ill, injured, suffering from a sudden onset of a medical condition, etc. Additionally, as used herein, the term "vehicle" may refer to any of a number of motorized transportation devices. A vehicle may be a car, truck, bus, train, boat, plane, etc. Additionally, as used herein, the term "wearable computing device" means a computer capable of being used while worn by the user, including a processor, a memory, an input, an output, and one or more programs or applications.

Figure 1:
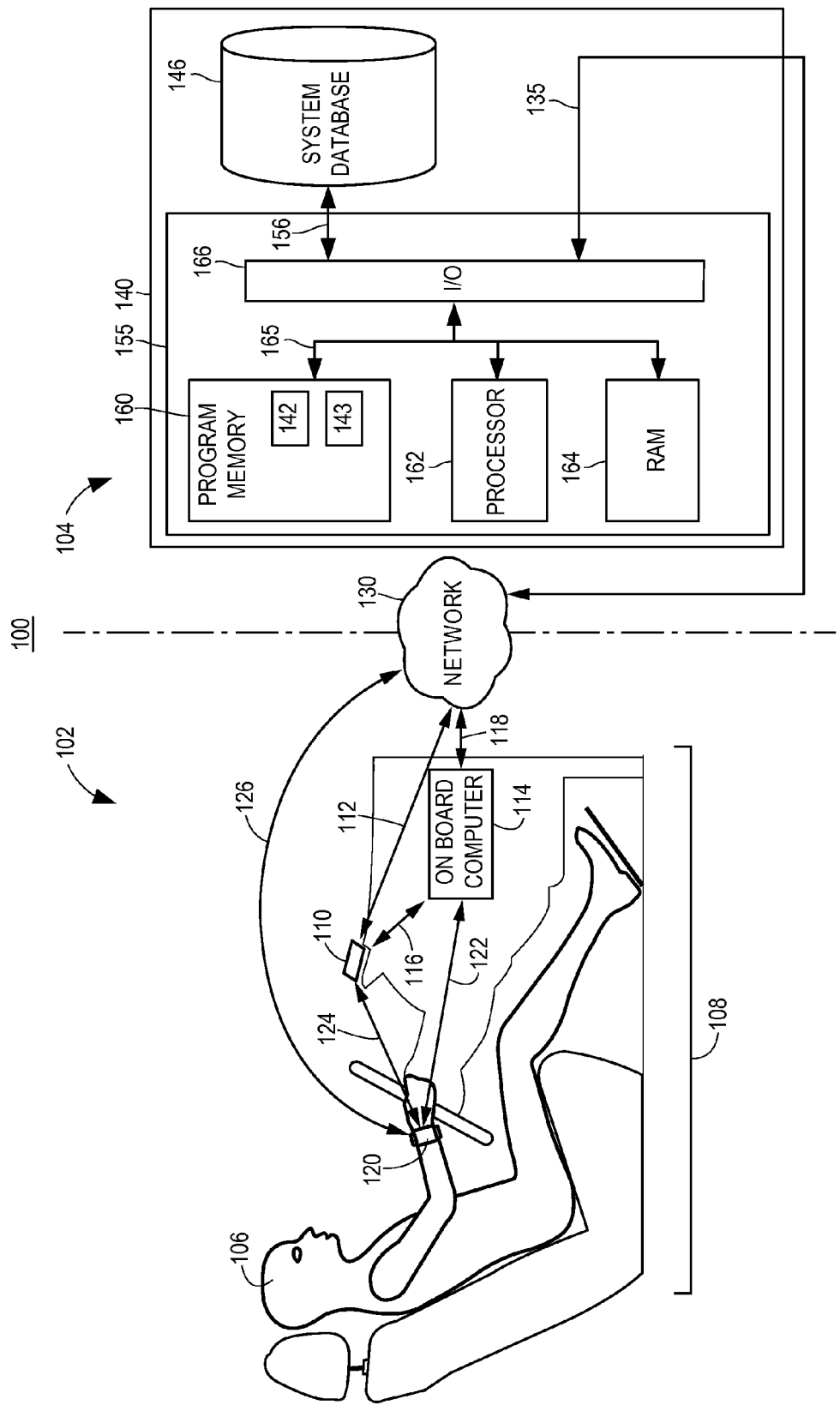
FIG. 1 illustrates a block diagram of a computer network, a computer server, a control device, and a wearable computing device on which an exemplary vehicle operator impairment alert system and method may operate in accordance with the described embodiments.

FIG. 1 illustrates a block diagram of an exemplary vehicle operator impairment alert system 100. The high-level architecture includes both hardware and software applications, as well as various data communications channels for communicating data between the various hardware and software components. The vehicle operator impairment alert system 100 may be roughly divided into front-end components 102 and back-end components 104. The front-end components 102 monitor a vehicle operator 106 for indications of impairment using data from various sensors (not shown) within a vehicle 108 (e.g., a car, truck, etc.). The front-end components 102 further alert the vehicle operator 106 using a wearable computing device 120 when impairment is detected. In some embodiments of the system, the front-end components 102 may communicate with the back-end components 104 via a network 130. The back-end components 104 may use one or more servers 140 to process the sensor data provided by the front-end components 102 to determine impairment of the vehicle operator 106 and communicate the determination of operator impairment to the front-end components 102 via the network 130. Additionally, or alternatively, the back-end components 104 may receive sensor data or determinations of impairment from the front-end components 102 and store the sensor data or determinations of impairment in a system database 146. The front-end components 102 or the back-end components 104 cause the wearable computing device 120 to present a haptic alert to the vehicle operator 106 following a determination of operator impairment.

The front-end components 102 are disposed within one or more wearable computing devices 120. Additionally, a portion of the front-end components 102 may be disposed within a control device consisting of one or more mobile devices 110 or one or more on-board computers 114. A mobile device 110 or on-board computer 114 may be permanently or removably installed in the vehicle 108. The mobile device 110, the on-board computer 114, or the wearable computing device 120 may interface with various sensors in the vehicle 108 (e.g., a braking sensor, a speedometer, a tachometer, an accelerometer, an optical sensor, etc.), which sensors may also be incorporated within or communicatively connected to the mobile device 110 (e.g., an accelerometer, a camera or other optical sensor, a microphone, etc.) or the wearable computing device 120 (e.g., an accelerometer, a galvanic skin response sensor, a heart rate monitor, etc.). The mobile device 110 or the on-board computer 114 may interface with the wearable computing device 120 to provide alerts to the vehicle operator 106. The mobile device 110, the on-board computer 114, or the wearable computing device 120 may further interface with various external output devices in the vehicle 108 such as one or more speakers or displays (not shown).

The on-board computer 114 may supplement the functions performed by the mobile device 110 or the wearable computing device 120 described herein by, for example, sending or receiving information to and from the mobile device 110 or the wearable computing device 120. In one embodiment, the on-board computer 114 may perform all of the functions of the mobile device 110 described herein, in which case no mobile device 110 may be present in the system 100. In another embodiment, the mobile device 110 may perform all of the functions of the on-board computer 114, in which case no on-board computer 114 may be present in the system 100. The mobile device 110, on-board computer 114, or wearable computing device 120 may communicate with the network 130 over links 112, 118, and 122, respectively. Additionally, the mobile device 110, on-board computer 114, and wearable computing device 120 may communicate with one another directly over links 116, 124, and 126.

The mobile device 110 may be either a general-use mobile personal computer, cellular phone, smart phone, tablet computer, or a dedicated vehicle operator impairment monitoring computer. The on-board computer 114 may be a general-use on-board computer capable of performing many functions relating to vehicle operation or a dedicated vehicle operator impairment monitoring computer. Further, the on-board computer 114 may be installed by the manufacturer of the vehicle 108 or as an aftermarket modification to the vehicle 108. Further, the mobile device 110, on-board computer 114, or wearable computing device 120 may be a thin-client device which outsources some or most processing to the server 140.

One or more vehicle operators 106 may be operating the vehicle 108. While shown in a slightly reclined sitting position, those of ordinary skill in the art will appreciate that the vehicle operator 106 could be situated in any number of ways (e.g., reclining at a different angle, standing, etc.) and operating the vehicle 108 using controls other than the steering wheel and pedals shown in FIG. 1 (e.g., one or more sticks, yokes, levers, etc.).

In some embodiments, the front-end components 102 communicate with the back-end components 104 via the network 130. The network 130 may be a proprietary network, a secure public internet, a virtual private network or some other type of network, such as dedicated access lines, plain ordinary telephone lines, satellite links, cellular data networks, combinations of these, etc. Where the network 130 comprises the Internet, data communications may take place over the network 130 via an Internet communication protocol. The back-end components 104 include a server 140. The server 140 may include one or more computer processors adapted and configured to execute various software applications and components of the vehicle operator impairment alert system 100, in addition to other software applications. The server 140 may further include a database 146, which may be adapted to store data related to the operation of the vehicle operator impairment alert system 100. Such data might include, for example, images, sensor inputs, data analyzed according to the methods discussed below, or other kinds of data pertaining to the vehicle operator impairment uploaded to the server 140 via the network 103. The server 140 may access data stored in the database 146 when executing various functions and tasks associated with the operation of the vehicle operator impairment alert system 100.

Although the vehicle operator impairment alert system 100 is shown to include one server 140, one mobile device 110, one wearable computing device 120, and one on-board computer 114 it should be understood that different numbers of servers 140, mobile devices 110, wearable computing devices 120, and on-board computers 114 may be utilized. For example, the system 100 may include a plurality of servers 140 and hundreds of mobile devices 110 or wearable computing devices 120, all of which may be interconnected via the network 130. As discussed above, the wearable computing device 120 may perform the various functions described herein in conjunction with the mobile device 110 or the on-board computer 114 or alone (in such cases, the mobile device 110 and the on-board computer 114 need not be present). Furthermore, the processing performed by the one or more servers 140 may be distributed among a plurality of servers 140 in an arrangement known as "cloud computing." This configuration may provide several advantages, such as enabling near real-time uploads and downloads of information as well as periodic uploads and downloads of information. This may in turn provide for a thin-client embodiment of the mobile device 110, on-board computer 114, or wearable computing device 120 discussed herein. Alternatively, the vehicle operator impairment alert system 100 may include only the front-end components 102. For example, a wearable computing device 120, together with a mobile device 110 or on-board computer 114, may perform all of the processing associated with receiving sensor data, determining whether the vehicle operator 106 is impaired, and alerting the vehicle operator 106. As such, the vehicle operator impairment alert system 100 may be a "stand-alone" system, neither sending nor receiving information over the network 130.

The server 140 may have a controller 155 that is operatively connected to the database 146 via a link 156. It should be noted that, while not shown, additional databases may be linked to the controller 155 in a known manner. The controller 155 may include a program memory 160, a processor 162 (which may be called a microcontroller or a microprocessor), a random-access memory (RAM) 164, and an input/output (I/O) circuit 166, all of which may be interconnected via an address/data bus 165. It should be appreciated that although only one microprocessor 162 is shown, the controller 155 may include multiple microprocessors 162. Similarly, the memory of the controller 155 may include multiple RAMs 164 and multiple program memories 160. Although the I/O circuit 166 is shown as a single block, it should be appreciated that the I/O circuit 166 may include a number of different types of I/O circuits. The RAM 164 and program memories 160 may be implemented as semiconductor memories, magnetically readable memories, or optically readable memories, for example. The controller 155 may also be operatively connected to the network 130 via a link 135.

Figure 2:
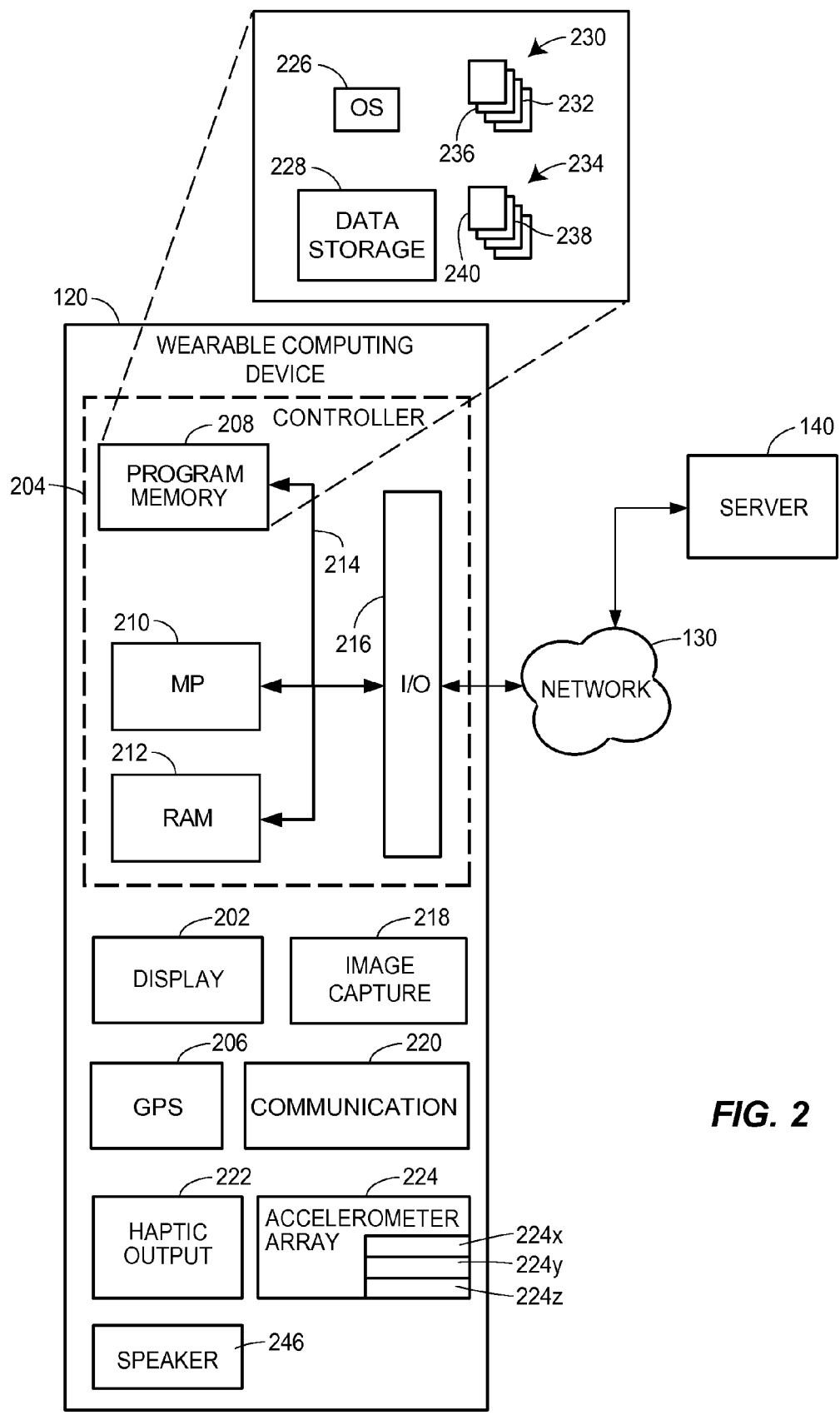
FIG. 2 illustrates a block diagram of an exemplary wearable computing device.

FIG. 2 illustrates a block diagram of a wearable computing device 120 for receiving and processing one or more transitory input signals and providing a haptic alert of operator impairment. The input signals may consist of sensor data signals from sensors incorporated within the wearable computing device 120. Additionally, or alternatively, the communication unit 220 may receive an input signal from one or more external sensors within the vehicle 108 or from the mobile device 110 or on-board computer 114. The input signals are processed by the controller 204 to determine whether an operator impairment condition exists. When operator impairment is determined, the wearable computing device 120 provides a haptic alert to the vehicle operator 106 using the haptic output unit 222. In addition to receiving sensor or other input signals, the wearable computing device 120 may transmit sensor data to one or more mobile devices 110, on-board computers 114, or servers 140 via a network 130. The wearable computing device 120 is capable of performing its functions while being worn by a vehicle operator 106. The following exemplary wearable devices may be wearable computing devices 120: computer-enhanced watches (smart watches), computer-enhanced eye glasses, computer-enhanced wireless headsets, clothing articles with embedded microprocessors, etc.

Similar to the controller 155, the controller 204 includes a program memory 208, a microcontroller or a microprocessor (MP) 210, a random-access memory (RAM) 212, and an input/output (I/O) circuit 216, all of which are interconnected via an address/data bus 214. The program memory 208 includes an operating system 226, a data storage 228, a plurality of software applications 230, and a plurality of software routines 234. The operating system 226, for example, may include one of a plurality of platforms such as the iOS®, Android™, Palm® OS, or Pebble™ OS, developed by Apple Inc., Google Inc., Palm Inc. (now Hewlett-Packard Company), and Pebble Technology Corp., respectively. The data storage 228 may include data such as user profiles and preferences, application data for the plurality of applications 230, routine data for the plurality of routines 234, and other data necessary to interact with a mobile device 110 or a server 140 through a network 130. In some embodiments, the controller 204 may also include, or otherwise be communicatively connected to, other data storage mechanisms (e.g., one or more hard disk drives, optical storage drives, solid state storage devices, etc.) that reside within the wearable computing device 114, mobile device 110, or on-board computer 114.

The communication unit 220 may communicate with one or more external sensors within the vehicle 108, mobile devices 110, on-board computers 114, or servers 140 via any suitable wireless communication protocol network, such as a wireless telephony network (e.g., GSM, CDMA, LTE, etc.), a Wi-Fi network (802.11 standards), a WiMAX network, a Bluetooth network, etc. Additionally, or alternatively, the communication unit 220 may also be capable of communicating using a near field communication standard (e.g., ISO/IEC 18092, standards provided by the NFC Forum, etc.). Further, the communication unit 220 may provide input signals to the controller 204 via the I/O circuit 216. The communication unit 220 may also transmit sensor data, device status information, control signals, or other output from the controller 204 to one or more external sensors within the vehicle 108, mobile devices 110, on-board computers 114, or servers 140.

The haptic output unit 222 may include a device capable of vibrating, poking, or otherwise tactilely notifying the vehicle operator 106. The haptic output unit 222 is controlled by the controller 204. When the controller 204 determines the vehicle operator 106 is impaired, the controller 204 may active the haptic output unit 222 in one or more manners to alert the vehicle operator 106 of the impairment. In addition to the haptic output unit 222, the wearable computing device 120 may include additional output units, such as a display 202 or a speaker 246. The additional output units may be used to provide auxiliary alerts to the vehicle operator 106 in conjunction with the haptic alert. The display 202 may include a liquid crystal display (LDC), light emitting diodes (LEDs), electrophoretic display, projector, head mounted display, etc.

The wearable computing device 120 may further include various input or sensing units, such as an accelerometer array 224, an optical sensor 218, a Global Positioning System (GPS) unit 206, a user-input device (not shown), etc. Of course, it will be appreciated that additional GPS units 206, optical sensors 218, or accelerometer arrays 224 may be added to the wearable computing device 120 or communicatively connected to the wearable computing device 120. Additional sensors may also be incorporated within or connected to a mobile device 110 or an on-board computer 114. Further, the mobile device 110, on-board computer 114, or wearable computing device 120 may also include (or be coupled to) other sensors (not shown) such as a thermometer, microphone, thermal image capture device, electroencephalograph (EEG), galvanic skin response (GSR) sensor, heart rate monitor, alcohol sensor, altimeter, other biometric sensors, etc. Unless context indicates otherwise, the GPS unit 206, optical sensor 218, accelerometer array 224, user-input device, and other sensors not shown may be referred to collectively as the "sensors" of the wearable computing device 120.

The accelerometer array 224 may be one or more accelerometers positioned to determine the force and direction of movements of the wearable computing device 120. In some embodiments, the accelerometer array 224 may include an X-axis accelerometer $224x$, a Y-axis accelerometer $224y$, and a Z-axis accelerometer $224z$ to measure the force and direction of movement in each dimension respectively. It will be appreciated by those of ordinary skill in the art that a three dimensional vector describing a movement of the wearable computing device 120 through three dimensional space can be established by combining the outputs of the X-axis, Y-axis, and Z-axis accelerometers $224x$, $y$, and $z$ using known methods. The resulting three dimensional vector or some component thereof may be used to determine movement or inactivity of the vehicle operator 106 to determine impairment. In a similar manner, the GPS unit 206 may be used to determine the movement of the vehicle 108 or vehicle operator 106 to determine whether the vehicle is in motion, stopped, accelerating or decelerating, centered within a lane, veering off course, swerving, etc.

An optical sensor 218 may observe the vehicle operator 106 and provide image data including head movements, eye movements, or other movements of the vehicle operator 106 to the controller 204. Additionally, or alternatively, one or more image capture devices may be incorporated within the mobile device 110 or may be connected to the on-board computer 114. Such optical sensor 218 or image capture devices may be positioned so as to observe the vehicle operator, the vehicle interior, the external environment of the vehicle (including a forward view, side views, or rear views). The controller may use the sensor data to determine head rotation frequency, head nodding, closed eyes, eye drooping, blink rate, eye scanning rate, gaze fixation, mirror checking, usage of vehicle devices (e.g., audio systems, environmental systems, navigation systems, etc.), or other cues that may indicate, alone or in combination, impairment of the vehicle operator 106.

A thermometer or thermal image capture device may be used to determine an abnormal vehicle operator 106 body temperature or a change in the vehicle operator's 106 body temperature (e.g., a decrease in body temperature may indicate that the vehicle operator 106 is drowsy or falling asleep, an elevated body temperature may indicate that the vehicle operator is ill). A microphone may be used to receive voice inputs as described below, and may also be used to detect irregularities in the voice of the vehicle operator 106 indicating that the vehicle operator 106 is under stress. An EEG may be used to determine whether the vehicle operator 106 is drowsy (i.e., the EEG shows that brain activity has decreased or matches known brain activity patterns associated with drowsiness), stressed, distracted, or otherwise impaired. A GSR sensor may be used to detect whether the vehicle operator 106 is stressed (i.e., that the conductance of the vehicle operator's 106 skin has varied from its normal level). A heart rate monitor may similarly be used to measure the vehicle operator's pulse in order to determine stress or other impairment. An alcohol sensor may detect whether there is alcohol in the vehicle operator's 106 breath or in the air inside the vehicle 108, which may indicate that the vehicle operator 106 is intoxicated. An altimeter may detect changes in altitude that may contribute to impairment of the vehicle operator 106.

A user-input device (not shown) may include a keyboard, a touch screen display, buttons, knobs, dials, microphones capable of receiving user voice input, or other device for receiving input or controls directly from the vehicle operator 106. The user-input device may be used to set, pause, cancel, adjust, arm, disable, or otherwise interact with the vehicle operator impairment alert system.

The one or more processors 210 may be adapted and configured to execute any one or more of the plurality of software applications 230 or any one or more of a plurality of software routines 234 residing in the program memory 204, in addition to other software applications. One of the plurality of applications 230 may be a client application 232 that may be implemented as a series of machine-readable instructions for performing the various tasks associated with implementing the vehicle operator impairment alert system as well as receiving information at, displaying information on, or transmitting information from the mobile device 110, on-board computer 114, wearable computing device 120, or server 140. The client application 232 may function to implement a stand-alone system or as a system wherein the front-end components 102 communicate with back-end components 104 as described herein. The client application 232 may include machine-readable instructions for implementing a user interface to allow a user to input commands to and receive information from vehicle operator impairment alert system 100. One of the plurality of routines may include an image capture routine 238 that coordinates with the optical sensor 218 to retrieve image data for use with one or more of the plurality of applications, such as the client application 232, or for use with other routines. Another routine in the plurality of routines may include an accelerometer routine 240 that determines the force and direction of movements of the mobile device 110, on-board computer 114, or wearable computing device 120. The accelerometer routine 240 may process data from the accelerometer array 224 to determine a vector describing the motion of the wearable computing device 120 for use with the client application 232. In some embodiments, the accelerometer routine 240 may use data pertaining to less than three axes, such as when determining when the vehicle 108 is braking.

A user may launch the client application 232 from the mobile device 110, on-board computer 114, or wearable computing device 120, to access the server 140 to implement the vehicle operator impairment alert system 100. Additionally, the customer or the user may also launch or instantiate any other suitable user interface application (e.g., a web browser 236, or any other one of the plurality of software applications 230) to access the server 140 to realize the vehicle operator impairment alert system 100.

The server 140 may further include a number of software applications, including software applications responsible for generating data content to be included in the web pages sent from the web server 143 to the mobile device 110, on-board computer 114, or wearable computing device 120. The software applications may be executed on the same computer processor as the web server application 143, or on different computer processors.

In embodiments where the mobile device 110, on-board computer 114, or wearable computing device 120 is a thin-client device, the server 140 may perform many of the processing functions remotely that would otherwise be performed by the mobile device 110, on-board computer 114, or wearable computing device 120. In such embodiments, the mobile device 110, on-board computer 114, or wearable computing device 120 may gather data from the sensors as described herein and send the data to the server 140 for remote processing. The server 140 may perform the analysis of the gathered data to determine whether the vehicle operator 106 may be impaired as described below. If the server 140 determines that the vehicle operator 106 may be impaired, the server 140 may command the wearable computing device 120 to alert the vehicle operator as described below. Additionally, the server 140 may generate metrics and suggestions based on the gathered data.

Figure 3:
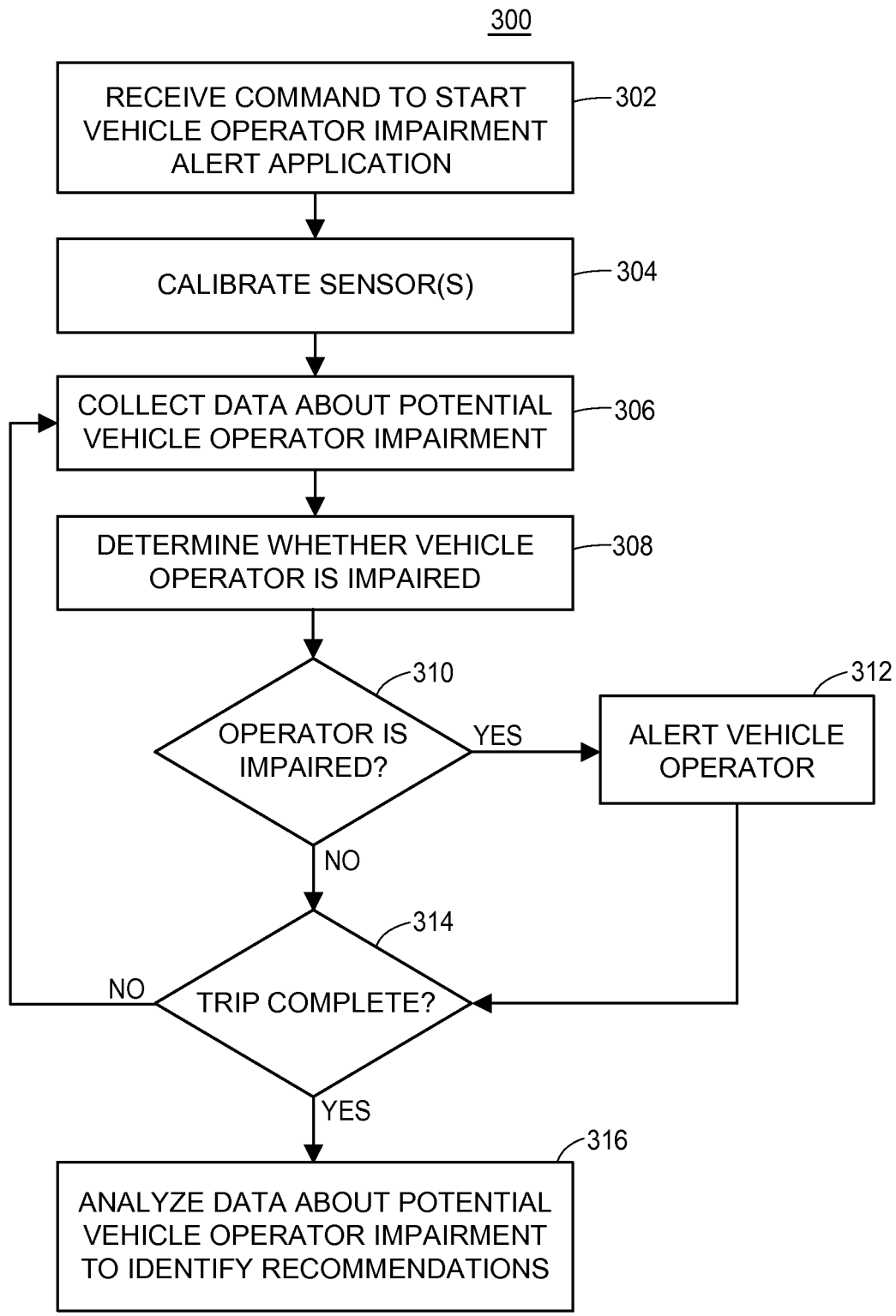
FIG. 3 depicts an exemplary vehicle operator impairment monitoring method for implementing the vehicle operator impairment alert system and method in accordance with the presently described embodiments.

FIG. 3 is a flow diagram depicting an exemplary embodiment of a vehicle operator impairment alert method 300 implemented by the vehicle operator impairment alert system 100. The method 300 may be performed by the mobile device 110, on-board computer 114, or wearable computing device 120 or any of these in conjunction with the server 140. Notwithstanding the preceding sentence, the step of alerting the vehicle operator (block 312) is performed by at least the haptic output unit 222 of the wearable computing device 120, although additional alerts may also be used in conjunction with the alert presented by the haptic output unit 222. The method 300 may be initiated by a command (block 302), following which the sensors may be calibrated (block 304). When in operation, the method 300 collects sensor data about the vehicle operator 106 (block 306), processes the sensor data to determine whether the operator is impaired (block 308), and alerts the vehicle operator 106 when an impairment is determined (block 312). Either during or after vehicle operation, sensor data or determinations of impairment may be stored and analyzed to identify operator impairment trends (block 316).

The command to start the vehicle operator impairment alert method 300 may be a user command received by the mobile device 110, on-board computer 114, or wearable computing device 120 via the client application 232. Alternatively or additionally, the command may be sent by the server 140 or may be generated automatically by the mobile device 110, on-board computer 114, or wearable computing device 120 after the meeting of a condition (e.g., the vehicle 108 has been started; the mobile device 110 is within a specified distance from the vehicle, a certain time, etc.).

Following initialization of the method 300, the sensors of the mobile device 110, on-board computer 114, or wearable computing device 120 may be calibrated (block 304). For example the optical sensor 218 or another image capture device may attempt to detect the face and eyes of the vehicle operator 106. Calibration may further entail adjusting the optical sensor 218 or image capture device to account for the skin tone, facial characteristics, etc. of the vehicle operator 106, ambient light in the vehicle, the background behind the vehicle operator 106, etc. The optical sensor 218 or image capture device may also be calibrated to attempt to detect a road in front of the vehicle, identify lane markings, identify other vehicles, detect coastlines or a water surface, or detect a horizon. Calibration may further entail adjusting the optical sensor 218 or image capture device to account for the color of a road, road conditions (e.g., a wet road from rain or an icy road from snow), the color of lane markings, average wave height, cloud cover, the time of day, ambient light, etc. The accelerometer array 224 may also be calibrated for constant vibration (e.g., the vibration caused by the engine of the vehicle 108) or other repetitive forces. Other sensors may similarly be calibrated upon initialization of the method 300 or at intervals during monitoring.

After calibration, the mobile device 110, on-board computer 114, or wearable computing device 120 may collect data about potential vehicle operator impairment using the various sensors communicatively connected thereto (block 306). Unmodified sensor data or determinations of operator impairment may also be stored or recorded in a log file by the mobile device 110, on-board computer 114, wearable computing device 120, or server 140. Sensor data received by sensors connected to one of the mobile device 110, on-board computer 114, or wearable computing device 120 may be communicated to another mobile device 110, on-board computer 114, or wearable computing device 120 for storing or processing. Sensor data may also be communicated to the server 140 for storing or processing. Sensor data may include a raw or modified output signal from any sensor incorporated within or communicatively connected to a mobile device 110, on-board computer 114, or wearable computing device 120.

Upon receiving the sensor data, the mobile device 110, on-board computer 114, wearable computing device 120, or server 140 processes the sensor data to determine whether the vehicle operator 106 is impaired (block 308). In one embodiment, the mobile device 110, on-board computer 114, or wearable computing device 120 may receive sensor data and transmit the data to the server 140 via network 130, which may be stored in program memory 160 or RAM 164 and processed using processor 162 according to program instructions stored in program memory 160. Alternatively, or in addition, the wearable computing device 120 may communicate sensor data to the mobile device 110 or on-board computer 114, where the sensor data may be processed or combined with other sensor data prior to transmission to the server 140. Sensor data may also be preprocessed by the mobile device 110, on-board computer 114, or wearable computing device 120 before being sent to another mobile device 110, on-board computer 114, or wearable computing device 120 or to the server 140 for processing to determine operator impairment. Such pre-processing may include processing image data to determine eye blinks, calculating a three-dimensional vector from accelerometer array 224 data, determining swerving or lane departure, etc.

In one embodiment, the method of determining impairment of a vehicle operator may include determining and logging a plurality of impairment indicators. Impairment indicators may be a series of measurements of conditions or characteristics pertaining to potential vehicle operator impairment derived from the sensors communicatively connected to the mobile device 110, on-board computer 114, or wearable computing device 120. Such measurements may be logged and stored in data storage 228 as an impairment indicator log, along with a timestamp to note the time of the measurement. The measurements may be logged periodically (e.g., every millisecond, every second, etc.) or conditionally on the occurrence of an event (e.g., an eye blink of a vehicle operator 106). Examples of impairment indicators include the following: vehicle operator blinks, frequency of vehicle operator blinks, duration of vehicle operator blinks, percent eye closed ("PERCLOS"), vehicle operator gaze location, vehicle operator gaze fixation, vehicle operator head nods, vehicle operator head rotations, vehicle operator arm movement, vehicle position relative to lane markings, lane deviation, failure to maintain lane centering, vehicle position relative to other vehicles, time to collision, time to brake, time to react, longitudinal vehicle control, vehicle braking, acceleration of the vehicle along any of multiple axes, etc.

Vehicle operator blinks may be determined using data from an optical sensor 218 or other camera within the vehicle 208 by watching the eyes of the vehicle operator 106 and determining when the visible size of the eyes decreases below a threshold value (e.g., two pixels) then increased above a threshold value after a blink. Frequency of vehicle operator blinks may then be calculated as a function of the time between blinks over a certain time period (e.g., 2 minutes, 5 minutes, etc.). Similarly, PERCLOS may be calculated as the sum of the duration of all blinks in a time period divided by the length of the time period. Vehicle operator gaze location may be determined by monitoring the eyes of the vehicle operator 106 with an optical sensor 218 or other camera within the vehicle 208. Vehicle operator gaze location may be used to determine when the vehicle operator 106 is looking at the road, mirrors, the dashboard, stereo or air conditioning controls, a mobile device, etc. and may be used to determine when gaze fixation has exceeded a threshold time period (e.g., 2 seconds, 5 seconds, etc.). Operator head nods and head rotations may likewise be measured by monitoring the face of the vehicle operator 106 with an optical sensor 218 or other camera within the vehicle 208 and detecting a vertical or horizontal acceleration of the vehicle operator's face exceeding threshold values. Vehicle operator arm movements and vehicle acceleration may be measured using the accelerometer array 224 to monitor forces in multiple axes. Vehicle acceleration may be used to determine hard braking, sharp acceleration, or swerving.

An optical sensor 218 or other camera within the vehicle 208 may also be used to monitor conditions on the road including identifying lane markings or other vehicles on the road by processing and comparing a series of images. Lane deviation may be determined by comparing the relative position of lane markings relative to image sensor input at multiple points in time. Time to collision may be determined by comparing vehicle position relative to other vehicles to determine when a decreasing time to collision indicates that the vehicle 108 may be too close to another vehicle, and vehicle acceleration measurements may be used in the determination. Alternatively or additionally, the data used to calculate time to collision may also be used to calculate similar metrics such as time to brake (i.e., the amount of time the vehicle operator 106 has to apply the brakes in order to prevent collision with an object) or time to react (i.e., the amount of time a vehicle operator 106 has to recognize an imminent collision and react to prevent it by swerving or applying the brakes). In addition to the data used to calculate time to collision, it may be advantageous to incorporate additional data into the calculation of time to brake and time to react such as the stopping capability of the vehicle 108, road conditions (e.g., wet, icy, unpaved, etc.), and the previously observed reaction time of the vehicle operator 106.

Figure 4:
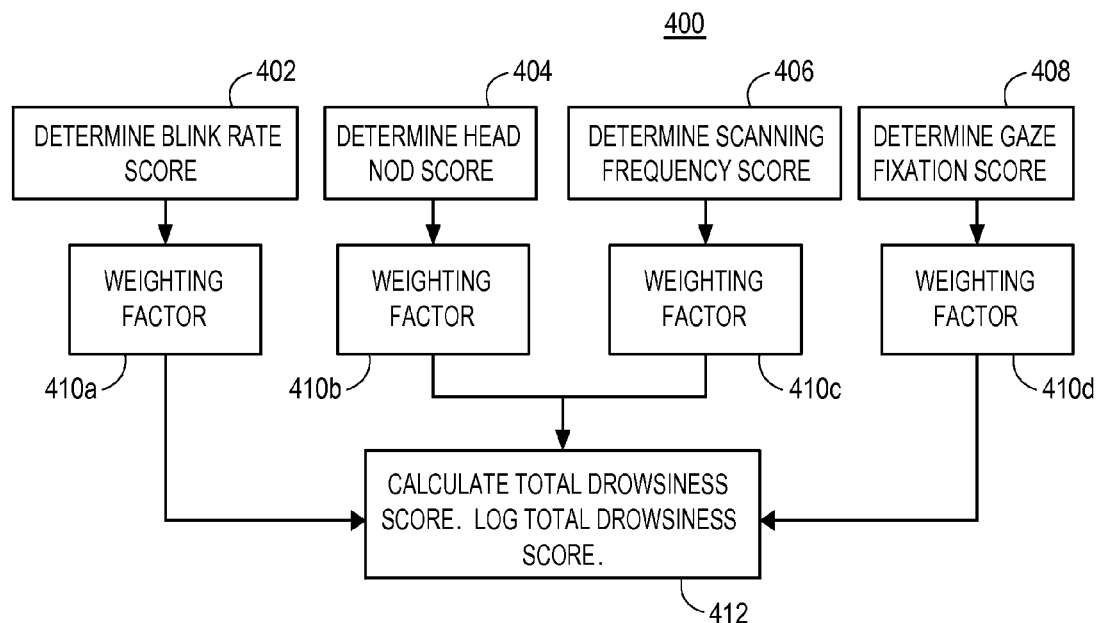
FIG. 4 depicts an exemplary vehicle operator drowsiness score determination method for implementing the vehicle operator impairment alert system in accordance with the presently described embodiments.
Figure 5:
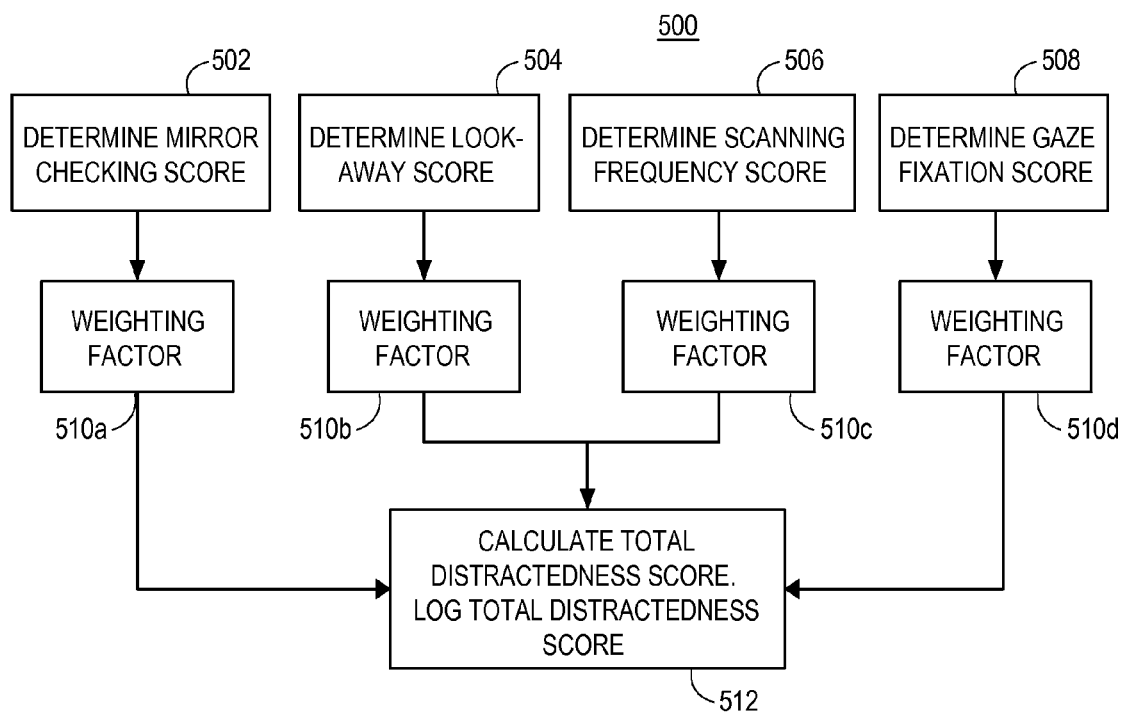
FIG. 5 depicts an exemplary vehicle operator distractedness score determination method for implementing the vehicle operator impairment alert system in accordance with the presently described embodiments.

After gathering impairment indicators, the vehicle operator impairment alert system 100 may analyze the impairment indicators to determine whether the vehicle operator 106 is impaired (e.g., having trouble staying awake, distracted, etc.) (block 308). Such analysis may be performed by the mobile device 110, on-board computer 114, wearable computing device 120, server 140, or a combination. Determining whether the vehicle operator 106 is impaired may include separate but complimentary determinations such as whether the vehicle operator 106 is drowsy, as shown in FIG. 4, or distracted, as shown in FIG. 5. It will be appreciated by those of ordinary skill in the art that these determinations may be made with a single process as well. Furthermore, the methods of determining vehicle operator impairment depicted in FIGS. 4 and 5 are exemplary only; alternative methods may be used to determine vehicle operator impairment.

FIG. 4 is a flow diagram depicting an exemplary embodiment of a vehicle operator drowsiness score determination 400 implemented by the vehicle operator impairment alert system 100 while determining whether the vehicle operator 106 is impaired at block 308. The method 400 determines a blink rate score, a head nod score, a scanning frequency score, and a gaze fixation score using one or more impairment indicators (blocks 402, 404, 406, and 408). Blink rate score may be determined by subtracting 1 point from a total score of 100 every time the blink rate of the vehicle operator 106 exceeds a threshold value (e.g., one blink per second) during a certain period of time (e.g., 1 minute, 2 minutes). Head nod score may be determined by subtracting 1 point from a total score of 100 every time a head nod is detected during a certain period of time. Scanning frequency score can be determined by subtracting 1 point from a total score of 100 every time the vehicle operator 106 fails to shift his or her gaze from one important area for vehicle operation (e.g., the road, mirrors, etc.) to another important area for vehicle operation within a threshold period of time (e.g., 5 seconds). For example, a vehicle operator 106 who is drowsy may not look from the road to check the mirrors and speed indicator with sufficient frequency. The gaze fixation score may be determined by subtracting 1 point from a total score of 100 every time gaze fixation is detected during a certain period of time. After determining scores for the individual impairment indicators as discussed above, the method 400 may multiply each score by a weighting factor 410*a*, *b*, *c*, or *d*. For example, if each score is weighted equally, the weighting factors 410*a-d* will be identical. However, it may be advantageous to weight one score higher than another. For example, head nods may indicate that the vehicle operator 106 is falling asleep and may be more important than scanning frequency or gaze fixation in determining whether the vehicle operator 106 is drowsy. In such an embodiment, the weighting factors 410*a-d* may be 0.25, 0.35, 0.20, and 0.20 respectively. In some embodiments, the weighting factors may be adjusted based on previous data for the user or for a large group of users. The weighting factors may be adjusted by one of the many known learning algorithms such as a support vector machine or neural network algorithms. The method 400 may then sum the weighted scores to determine a total drowsiness score (block 412). The total drowsiness score may be logged with a timestamp and stored in data storage 228 or sent to the server 140 for remote storage. Referring again to FIG. 3, if the drowsiness score is below an impairment threshold value (e.g., 90 out of 100), the vehicle operator impairment alert system 100 may determine that the vehicle operator 106 is impaired (block 310).

FIG. 5 is a flow diagram depicting an exemplary embodiment of a vehicle operator distractedness score determination method 500 implemented by the vehicle operator impairment alert system 100 while determining whether the vehicle operator 106 is impaired at block 308. The method 500 may determine a mirror checking score, look-away score, scanning frequency score, and gaze fixation score using one or more impairment indicators (block 502, 504, 506, and 508). A mirror checking score may be determined by subtracting 1 point from a total score of 100 every time the vehicle operator fails to look at a mirror within a threshold period of time over a certain period of time (e.g., 1 minute, 2 minutes). Look-away score may be determined by subtracting 1 point from a total score of 100 every time the frequency or duration of a look-away exceeds a threshold period of time during a certain period of time. Look-aways may include head rotations and gaze location on a distraction (e.g., the stereo, a mobile phone, etc.). Scanning frequency score can be determined by subtracting 1 point from a total score of 100 every time the vehicle operator 106 fails to shift his or her gaze from one important area for vehicle operation (e.g., the road, mirrors, etc.) to another important area for vehicle operation within a threshold period of time (e.g., 5 seconds) within a certain period of time. For example, a vehicle operator 106 who is distracted may not look from the road to check the mirrors and speed indicator with sufficient frequency. The gaze fixation score may be determined by subtracting 1 point from a total score of 100 every time gaze fixation is detected during a certain period of time. After determining scores for the individual impairment indicators as discussed above, the method 500 may multiply each score by a weighting factor 510*a, b, c*, or *d* similar to the weighting factors for the vehicle operator drowsiness detection method 400 discussed above. The weighting factors may likewise be adjusted by one of the many known learning algorithms such as a support vector machine or neural network algorithms. The method 500 may then sum the weighted scores to determine a total distractedness score (block 512). The total distractedness score may be logged with a timestamp and stored in data storage 228 or sent to the server 140 for remote storage. Referring again to FIG. 3, if the distractedness score is below an impairment threshold value (e.g., 90 out of 100), the vehicle operator impairment alert system 100 may determine that the vehicle operator 106 is impaired (block 310).

Alternatively, it will be understood that instead of a weighted sum adding up to a total drowsiness score or distractedness score, either may instead be a weighted sum that is subtracted from a maximum score. In such a case, the individual impairment indicator scores discussed above may be calculated differently. While FIGS. 4 and 5 describe embodiments of methods 400 and 500 using weighted sums to determine total drowsiness or distractedness scores, respectively, other mathematical operations may be used to determine the total drowsiness or distractedness scores. While the exemplary embodiment discussed above uses a 100 point scale, it will be appreciated that a 100 point scale is just one of many point scales that could be used (e.g., 1 point scale, 50 point scale, 220 point scale, etc.). Additional impairment indicators may be used in the determination of the drowsiness score or distractedness scores. For example, slow lane deviation, failure to maintain lane centering, time to collision below a threshold, hard brake, sharp acceleration, or swerve impairment indicators may be added to the calculation of the drowsiness or distractedness scores in a manner similar to that described above in connection with FIGS. 4 and 5. Additionally, or alternatively, impairment scores other than drowsiness and distractedness scores may be determined (e.g., intoxication, agitation, etc.).

The vehicle operator impairment alert system 100 may permit the user to adjust the sensitivity setting for either or both of the drowsiness or distractedness scores. Additionally or alternatively, the vehicle operator impairment alert system 100 may include one of the many known learning algorithms such as support vector machine or neural network algorithms to adjust the individual threshold values discussed in connection with FIGS. 4 and 5 (e.g., the blink rate threshold of one blink per second). The learning algorithm may operate in connection with the server 140 to adjust the individual threshold level based on calculations performed using aggregated data from some or all of the mobile devices 110, on-board computers 114, or wearable computing devices 120 in the vehicle operator impairment alert system 100.

Referring again to FIG. 3, when the vehicle operator impairment alert system 100 has determined that the vehicle operator 106 is impaired, the vehicle operator impairment alert system 100 alerts the vehicle operator 106 using a haptic alert (block 312). The alert comprises a haptic alert using the haptic output unit 222 of the wearable computing device 120 (block 312). The haptic alert may be a vibration, poking, or other tactile notification and may be steady, periodically repeating, or variable. The haptic output unit may be controlled by the wearable computing device 120 through one or more software application 230 or software routine 234. Alternatively, the haptic output unit may be controlled by the mobile device 110, on-board computer 114, or server 140. Additionally, the haptic alert may be customizable or programmable either using the wearable computing device 120 or using the mobile device 110, on-board computer 114, or server 140. Providing a haptic alert directly to the vehicle operator 106 may improve operator response in some cases, particularly when an impaired vehicle operator is drowsy or distracted. A wearable computing device 120 may, in many cases, present a better haptic alert than a mobile device 110 or an on-board system. Because it is wearable, a wearable computing device 120 may be in more regular contact with a vehicle operator 106, thereby facilitating the delivery of a haptic alert.

Figure 6:
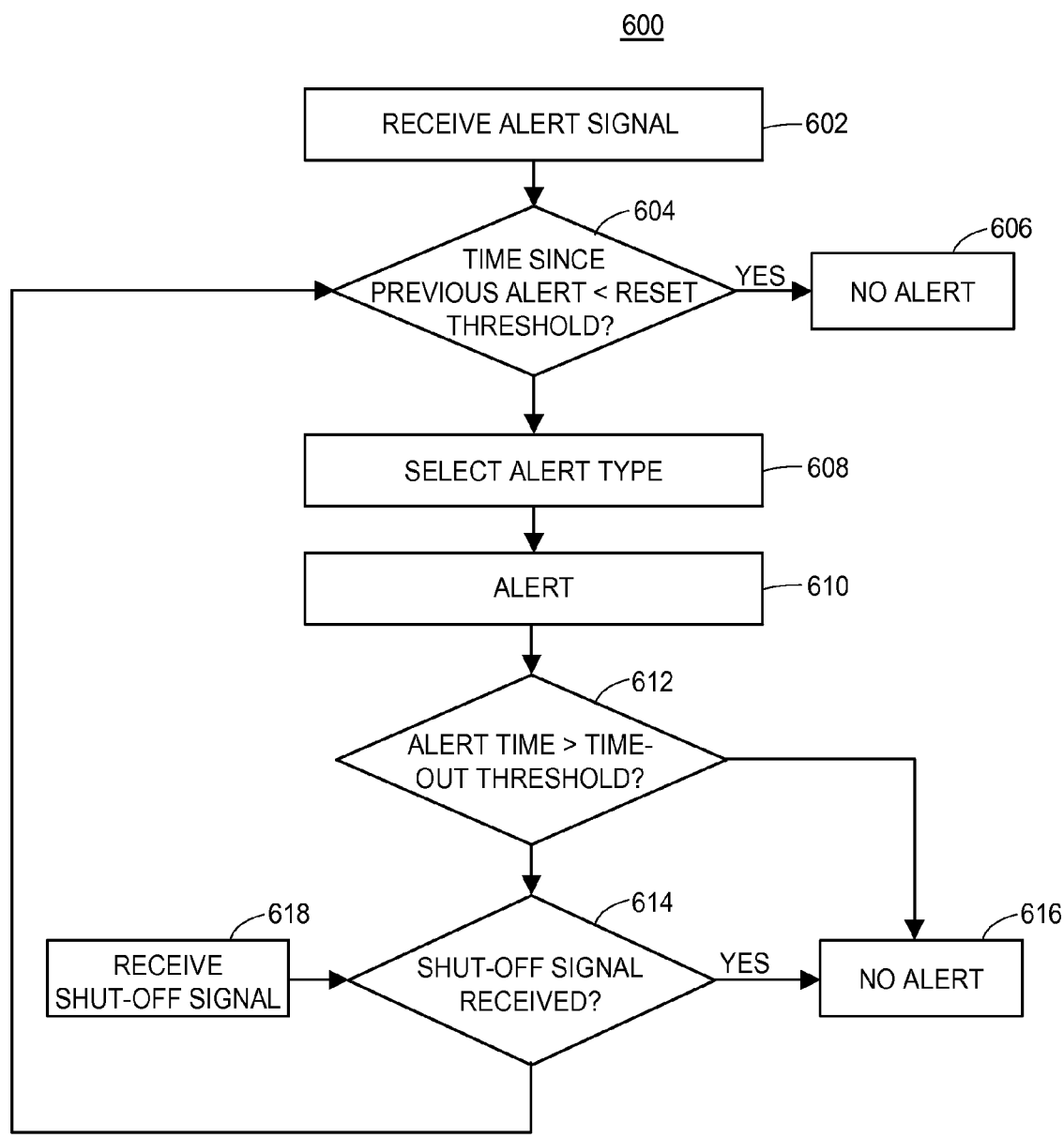
FIG. 6 depicts an exemplary vehicle operator impairment alert method for implementing the vehicle operator impairment alert system in accordance with the presently described embodiments.

FIG. 6 is a flow diagram depicting an exemplary embodiment of the vehicle operator impairment alert method. Upon a determination that the vehicle operator 106 is impaired (block 310), an alert signal may be sent to the wearable computing device 120 or to a client application 232 or software routine 234 (block 602). Alternatively, the alert signal may be sent to a mobile device 110, on-board computer 114, or server 140, and the alert may be directly controlled by such device. Additional alert signals may be sent to a mobile device 110 or on-board computer 114 if additional alerts may be provided. In one embodiment, a reset threshold may be used to ensure a reset period (e.g., 30 seconds, 1 minute, etc.) between alerts by comparing the time elapsed since the previous alert with the reset threshold (block 604). If the time elapsed since the previous alert is less than the reset threshold, then no alert is presented in response to the alert signal (block 606). If the time elapsed since the previous alert is greater than or equal to the reset threshold, then a haptic alert is delivered to the vehicle operator 106. In one embodiment, the type of haptic alert to be delivered may be selected from among various alternatives (e.g., steady, periodically repeating, or variable vibration, poking, or other tactile notification, etc.) based on user preferences, sensor data, or other factors (block 608). A haptic alert is then delivered to the vehicle operator 106 by the haptic output unit 222 of the wearable computing device 120 (block 610). The haptic alert may continue until a time-out threshold (e.g., 10 seconds, 20 seconds, etc.) has been reached (block 612) or until disabled by the vehicle operator 106 (block 614). If the duration the haptic alert exceeds the time-out threshold, then the haptic alert is disabled (block 616). The vehicle operator 106 may also disable the haptic alert by providing a shut-off input, such as depressing a button on the wearable computing device 120, touching the display 202, shaking or moving the wearable computing device 120 (such as by shaking a wrist or head), speaking a command, stopping the vehicle 108, etc. (block 618). If a shut-off signal is received, then the haptic alert is disabled (616). Until the haptic alert is disabled by either the vehicle operator 106 or upon reaching the time-out threshold, the haptic output unit 222 continues to deliver a haptic alert to the vehicle operator 106 (block 610).

It will be understood that this method 600 may be performed by either hardware or software interacting with hardware and by a variety of methods, which may include counting up to or down from any threshold, with appropriate modifications. Additionally, the steps presented in the exemplary embodiment may be performed in a different order, combined, or eliminated without materially modifying the method of providing a haptic alert using a wearable computing device 120. Furthermore, additional audible, visual, or tactile alerts may be added to supplement the haptic alert delivered by the wearable computing device 120. Audible alerts may include chimes, claxons, sirens, etc. or custom recorded sounds such as sound clips or ringtones. Visual alerts may include displaying icons on the display 202, displaying flashing icons on the display 202, or activating one or more lights (not shown) coupled to the mobile device 110 or on-board computer 114.

In one exemplary embodiment of the method 300, a wearable computing device 120 such as a smart watch may provide preprocessed sensor data to a mobile device 110 such as a smart phone, with additional sensor data provided by an on-board computer 114. The mobile device 110 may then process the sensor data received from the on-board computer 114 and the wearable computing device 120 in combination with data from sensors incorporated within or connected to the mobile device. Alternatively, the mobile device 110 may transmit the sensor data to a server 140 via a network 130. The mobile device 110 may alternate between processing the sensor data and transmitting the sensor data to the server 140 depending on factors such as the amount of sensor data available, the quality of the connection 118 between the mobile device 110 and the network 130, the load on the server 140, etc. The sensor data may then be processed by the mobile device 110 or the server 114 to determine whether the vehicle operator 106 is impaired, as described above. If the sensor data is processed by the server 140, the determination is then transmitted to the mobile device 110 via the network 130. If the vehicle operator 106 is determined to be impaired, the mobile device 110 then instructs the wearable computing device 120 to alert the vehicle operator 106 using the haptic output unit 222. Additional alerts may be provided by the mobile device 110, on-board computer 114, or wearable computing device 120, which may include audible alerts from the speaker 246 or other speakers within the vehicle, visual alerts from the display 202 or other displays controlled by the mobile device 110 or on-board computer 114, etc. For example, the display 202 may alternate between various images to produce a flashing alert. A short text message (such as "WARNING") may also be displayed on the display 202.

The vehicle operator impairment alert system 100 may continue to gather and analyze data while a particular trip is ongoing (block 314). The trip may become completed by a user command (e.g., the user selects a "Stop" button on the mobile device 110, on-board computer 114, or wearable computing device 120) or automatically (e.g., the on-board computer 114 detects that the engine of the vehicle 108 has stopped). When the trip is complete, the vehicle operator impairment alert system 100 may analyze the data collected during the just completed trip along with data from previous trips to provide metrics and suggestions to the user. For example, the vehicle operator impairment alert system 100 may analyze the impairment scores of a user with the time and date of each trip to determine patterns in the user's impairment. For example, the vehicle operator impairment alert system 100 may analyze thirty trips over the course of two weeks and determine that the user tends to be most impaired around the hours of 12 P.M. and 6 P.M. Accordingly, the vehicle operator impairment alert system 100 may recommend that the user avoid vehicle operation around the hours of 12 P.M. and 6 P.M. or take other ameliorative actions (e.g., drinking a caffeinated beverage shortly before operating the vehicle at high impairment times, removing distractions by turning off the stereo at high impairment times).

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Additionally, certain embodiments are described herein as including logic or a number of routines, subroutines, applications, or instructions. These may constitute either software (code embodied on a non-transitory, tangible machine-readable medium) or hardware. In hardware, the routines, etc., are tangible units capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connect the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor-implemented. For example, at least some of the operations of a method may be performed by one or more processors or processor-implemented hardware modules. The performance of certain of the operations may be distributed among the one or more processors, not only residing within a single machine, but deployed across a number of machines. In some example embodiments, the processor or processors may be located in a single location (e.g., within a home environment, an office environment or as a server farm), while in other embodiments the processors may be distributed across a number of locations.

The performance of certain of the operations may be distributed among the one or more processors, not only residing within a single machine, but deployed across a number of machines. In some example embodiments, the one or more processors or processor-implemented modules may be located in a single geographic location (e.g., within a home environment, an office environment, or a server farm). In other example embodiments, the one or more processors or processor-implemented modules may be distributed across a number of geographic locations.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the description. This description, and the claims that follow, should be read to include one or at least one and the singular also includes the plural unless it is obvious that it is meant otherwise.

This detailed description is to be construed as exemplary only and does not describe every possible embodiment, as describing every possible embodiment would be impractical, if not impossible. One could implement numerous alternate embodiments, using either current technology or technology developed after the filing date of this application.

Upon reading this disclosure, those of skill in the art will appreciate still additional alternative structural and functional designs for system and a method for assigning mobile device data to a vehicle through the disclosed principles herein. Thus, while particular embodiments and applications have been illustrated and described, it is to be understood that the disclosed embodiments are not limited to the precise construction and components disclosed herein. Various modifications, changes and variations, which will be apparent to those skilled in the art, may be made in the arrangement, operation and details of the method and apparatus disclosed herein without departing from the spirit and scope defined in the appended claims.

The particular features, structures, or characteristics of any specific embodiment may be combined in any suitable manner and in any suitable combination with one or more other embodiments, including the use of selected features without corresponding use of other features. In addition, many modifications may be made to adapt a particular application, situation or material to the essential scope and spirit of the present invention. It is to be understood that other variations and modifications of the embodiments of the present invention described and illustrated herein are possible in light of the teachings herein and are to be considered part of the spirit and scope of the present invention. By way of example, and not limitation, the present disclosure contemplates at least the following aspects:

1. A computer-implemented method for alerting a vehicle operator of operator impairment comprising: receiving sensor data regarding the potential impairment of the vehicle operator from one or more sensors; determining, using one or more processors, whether the sensor data indicates the vehicle operator is impaired; presenting, using one or more processors, an impairment alert to the vehicle operator that includes a haptic alert; and presenting the impairment alert using a wearable computing device worn by the vehicle operator.

2. The method according to aspect 1, further comprising presenting the impairment alert using a smart watch.

3. The method according to either aspect 1 or aspect 2, further comprising causing the smart watch to provide sensor data regarding the vehicle operator to a control device within the vehicle and wherein the control device uses one or more processors to receive the sensor data from the watch and one or more other sensors, determine whether the vehicle operator is impaired, and instruct the watch to present the haptic alert to the vehicle operator.

4. The method according to any one of the preceding aspects, further comprising terminating the impairment alert by one or more of the following actions by the vehicle operator: depressing a button on the watch, performing a physical movement of the wrist, touching the watch, or speaking a command.

5. The method according to any one of the preceding aspects, further comprising causing a control device within the vehicle to receive the sensor data, determine whether the sensor data indicates the vehicle operator is impaired, and control the presentation of impairment alerts by the wearable computing device worn by the vehicle operator.

6. The method according to any one of the preceding aspects, further comprising receiving at the control device sensor data regarding one or more of the following: a vehicle operator head nod, a vehicle operator scanning frequency, a vehicle operator gaze fixation, a vehicle operator mirror checking, a vehicle operator head rotation, a vehicle operator arm movement, a vehicle operator skin conductivity, a vehicle operator temperature, a vehicle operator pulse rate, a vehicle lane deviation, a vehicle swerving, a vehicle lane centering, a vehicle acceleration along a single axis or multiple axes, or a vehicle distance to other objects.

7. The method according to any one of the preceding aspects, wherein the control device is a mobile telephone.

8. The method according to any one of the preceding aspects, further comprising causing the control device to transmit the sensor data to one or more servers through a network and determining, with the one or more servers, whether the sensor data indicates the vehicle operator is impaired.

9. The method according to any one of the preceding aspects, further comprising terminating the alert with a first timer element after a specified time-out period and preventing, with a second timer element, multiple alerts within a specified reset period.

10. The method according to any one of the preceding aspects, further comprising selecting one or more impairment alerts from a database of potential responses based on the sensor data and presenting the one or more selected impairment alerts to the vehicle operator.

11. A computer system for alerting a vehicle operator of operator impairment comprising: one or more processors; one or more sensors; one or more wearable computing devices; and a program memory storing executable instructions that when executed by the one or more processors cause the computer system to: receive sensor data regarding the vehicle operator from the one or more sensors; determine, using one or more processors, whether the vehicle operator is impaired based on the received sensor data; and deliver a haptic alert to the vehicle operator using the one or more wearable computing devices when the vehicle operator is determined to be impaired.

12. The computer system according to aspect 11, wherein the computer system further includes a control device communicatively coupled with the wearable computing device that executes the executable instructions stored in the program memory using the one or more processors to: receive the sensor data; determine whether the vehicle operator is impaired based on the sensor data; and cause the wearable computing device to deliver the haptic alert to the vehicle operator when the vehicle operator is determined to be impaired.

13. The computer system according to either aspect 11 or aspect 12, wherein the control device is connected to one or more networked servers and wherein the networked servers determine, using one or more processors, whether the vehicle operator is impaired based on the sensor data.

14. The computer system according to any one of aspects 11-13, wherein the wearable computing device used to deliver the haptic alert is a smart watch.

15. The computer system according to any one of aspects 11-14, wherein the watch provides sensor data regarding the vehicle operator, including one or more of the following: accelerometer data, pulse data, skin resistivity data, thermal data, and optical data.

16. A tangible, non-transitory computer-readable medium storing instructions that when executed by one or more processors of a computer system cause the computer system to: monitor a vehicle operator using sensor data from one or more sensors; determine whether the vehicle operator is impaired based on the received sensor data; and cause one or more wearable computing devices to provide a haptic alert to the vehicle operator when the vehicle operator is determined to be impaired.

17. The tangible, non-transitory computer-readable medium according to aspect 16, further comprising executable instructions that when executed by the one or more processors cause the haptic alert to be provided to the vehicle operator by a smart watch.

18. The tangible, non-transitory computer-readable medium according to either aspect 16 or aspect 17, wherein the executable instructions that when executed by the one or more processors cause the computer system to monitor the vehicle operator and determine whether the vehicle operator is impaired are executed by one or more processors of a control device within the vehicle.

19. The tangible, non-transitory computer-readable medium according to any one of aspects 16-18, wherein the executable instructions that when executed by the one or more processors cause the computer system to monitor the vehicle operator and determine whether the vehicle operator is impaired are executed by one or more processors of one or more networked servers.

20. The tangible, non-transitory computer-readable medium according to any one of aspects 16-19, wherein the executable instructions that when executed by the one or more processors cause the computer system to monitor the vehicle operator include executable instructions that when executed by the one or more processors cause the computer system to monitor the vehicle operator using one or more of the following sensor data from the watch: accelerometer data, pulse data, skin resistivity data, thermal data, or optical data.

What is claimed:

1. A computer-implemented method for alerting a vehicle operator of operator impairment comprising:
   receiving sensor data regarding the potential impairment of the vehicle operator from one or more sensors;
   determining, using one or more processors, whether the sensor data indicates the vehicle operator is impaired by (i) calculating a plurality of impairment indicator scores using the received sensor data, (ii) calculating an impairment score associated with a type of impairment based upon the plurality of impairment indicator scores, and (iii) comparing the impairment score to a threshold value to determine whether the vehicle operator is impaired;
   selecting, using one or more processors, one or more impairment alerts from a database of potential responses based on the sensor data when the vehicle operator is determined to be impaired, wherein selecting the one or more impairment alerts includes selecting a haptic alert from a plurality of haptic alerts from the database of potential responses; and
   presenting the one or more selected impairment alerts to the vehicle operator, wherein the haptic alert is presented using a wearable computing device worn by the vehicle operator and wherein presenting the one or more impairment alerts include automatically preventing presentation of a subsequent alert within a predetermined reset period following presentation of the one or more impairment alerts.

2. The method of claim 1, further comprising presenting the one or more impairment alerts using a smart watch.

3. The method of claim 2, further comprising causing the smart watch to provide sensor data regarding the vehicle operator to a control device within the vehicle and wherein the control device uses one or more processors to receive the sensor data from the watch and one or more other sensors, determine whether the vehicle operator is impaired, and instruct the watch to present the haptic alert to the vehicle operator.

4. The method of claim 2, further comprising terminating the one or more impairment alerts by performing a physical movement of the wrist.

5. The method of claim 1, further comprising causing a control device within the vehicle to receive the sensor data, determine whether the sensor data indicates the vehicle operator is impaired, and control the presentation of impairment alerts by the wearable computing device worn by the vehicle operator.

6. The method of claim 5, further comprising receiving at the control device sensor data regarding one or more of the following: a vehicle operator head nod, a vehicle operator scanning frequency, a vehicle operator gaze fixation, a vehicle operator mirror checking, a vehicle operator head rotation, a vehicle operator arm movement, a vehicle operator skin conductivity, a vehicle operator temperature, a vehicle operator pulse rate, a vehicle lane deviation, a vehicle swerving, a vehicle lane centering, a vehicle acceleration along a single axis or multiple axis, or a vehicle distance to other objects.

7. The method of claim 5, wherein the control device is a mobile telephone.

8. The method of claim 5, further comprising causing the control device to transmit the sensor data to one or more servers through a network and determining, with the one or more servers, whether the sensor data indicates the vehicle operator is impaired.

9. The method of claim 1, further comprising terminating the one or more impairment alerts with a first timer element after a specified time-out period.

10. The method of claim 1, further comprising:
    receiving a first set of data from the one or more sensors in the vehicle;
    determining one or more calibration adjustments to the received first set of data to delineate features of the vehicle operator or the vehicle environment; and
    applying the one or more calibration adjustments to the received sensor data prior to determining whether the sensor data indicates the vehicle operator is impaired.

11. A computer system for alerting a vehicle operator of operator impairment comprising:
    one or more processors;
    one or more databases storing information regarding potential responses to impairments;
    one or more sensors;
    one or more wearable computing devices; and
    a program memory storing executable instructions that when executed by the one or more processors cause the computer system to:
      receive sensor data regarding the vehicle operator from the one or more sensors;
      determine whether the vehicle operator is impaired based on the received sensor data by (i) calculating a plurality of impairment indicator scores using the received sensor data, (ii) calculating an impairment score associated with a type of impairment based upon the plurality of impairment indicator scores, and (iii) comparing the impairment score to a threshold value to determine whether the vehicle operator is impaired;
      select one or more impairment alerts from the one or more databases based on the sensor data when the vehicle operator is determined to be impaired, wherein selecting the one or more impairment alerts includes selecting a haptic alert from a plurality of haptic alerts from the database of potential responses; and
      deliver the one or more selected impairment alerts to the vehicle operator, wherein the haptic alert is delivered to the vehicle operator using the one or more wearable computing devices and wherein delivering the haptic alert includes automatically preventing delivery of a subsequent alert within a predetermined reset period following delivery of the haptic alert.

12. The computer system of claim 11, wherein the computer system further includes a control device communicatively coupled with the wearable computing device that executes the executable instructions stored in the program memory using the one or more processors to:
    receive the sensor data;
    determine whether the vehicle operator is impaired based on the sensor data; and
    cause the wearable computing device to deliver the haptic alert to the vehicle operator when the vehicle operator is determined to be impaired.

13. The computer system of claim 12, wherein the control device is connected to one or more networked servers and wherein the networked servers determine, using one or more processors, whether the vehicle operator is impaired based on the sensor data.

14. The computer system of claim 11, wherein the wearable computing device used to deliver the haptic alert is a smart watch.

15. The computer system of claim 14, wherein the watch provides sensor data regarding the vehicle operator, including one or more of the following: accelerometer data, pulse data, skin resistivity data, thermal data, and optical data.

16. A tangible, non-transitory computer-readable medium storing instructions that when executed by one or more processors of a computer system cause the computer system to:
   monitor a vehicle operator using sensor data from one or more sensors;
   determine whether the vehicle operator is impaired based on the received sensor data by (i) calculating a plurality of impairment indicator scores using the received sensor data, (ii) calculating an impairment score associated with a type of impairment based upon the plurality of impairment indicator scores, and (iii) comparing the impairment score to a threshold value to determine whether the vehicle operator is impaired;
   select one or more impairment alerts from a database of potential responses based on the received sensor data when the vehicle operator is determined to be impaired, wherein selecting the one or more impairment alerts includes selecting a haptic alert from a plurality of haptic alerts from the database of potential responses; and
   cause the selected one or more impairment alerts to be provided to the vehicle operator, wherein one or more wearable computing devices are caused to provide the haptic alert to the vehicle operator and wherein the one or more wearable computing devices are automatically prevented from providing a subsequent alert within a predetermined reset period following provision of the haptic alert.

17. The tangible, non-transitory computer-readable medium of claim 16, further comprising executable instructions that when executed by the one or more processors cause the haptic alert to be provided to the vehicle operator by a smart watch.

18. The tangible, non-transitory computer-readable medium of claim 17, wherein the executable instructions that when executed by the one or more processors cause the computer system to monitor the vehicle operator and determine whether the vehicle operator is impaired are executed by one or more processors of a control device within the vehicle.

19. The tangible, non-transitory computer-readable medium of claim 17, wherein the executable instructions that when executed by the one or more processors cause the computer system to monitor the vehicle operator and determine whether the vehicle operator is impaired are executed by one or more processors of one or more networked servers.

20. The tangible, non-transitory computer-readable medium of claim 17, wherein the executable instructions that when executed by the one or more processors cause the computer system to monitor the vehicle operator include executable instructions that when executed by the one or more processors cause the computer system to monitor the vehicle operator using one or more of the following sensor data from the watch: accelerometer data, pulse data, skin resistivity data, thermal data, or optical data.

* * * * *